United States Patent
Sagi-Dolev

(10) Patent No.: US 8,196,482 B2
(45) Date of Patent: Jun. 12, 2012

(54) APPARATUS FOR EFFICIENT RESOURCE SHARING

(75) Inventor: Alysia M. Sagi-Dolev, Palo Alto, CA (US)

(73) Assignee: Qylur Security Systems, Inc., Palo Alto, CA (US)

(*) Notice: Subject to any disclaimer, the term of this patent is extended or adjusted under 35 U.S.C. 154(b) by 889 days.

(21) Appl. No.: 12/025,688

(22) Filed: Feb. 4, 2008

(65) Prior Publication Data

US 2008/0196518 A1 Aug. 21, 2008

Related U.S. Application Data

(63) Continuation-in-part of application No. 11/223,494, filed on Sep. 9, 2005, now Pat. No. 7,337,686.

(60) Provisional application No. 60/680,313, filed on May 13, 2005, provisional application No. 60/608,689, filed on Sep. 10, 2004.

(51) Int. Cl.
    *G01N 19/00* (2006.01)
(52) U.S. Cl. ......... 73/865.8; 73/865.6; 73/866; 340/521
(58) Field of Classification Search ............... 73/865.8, 73/865.6, 865.9, 866; 340/521, 573.1
    See application file for complete search history.

(56) References Cited

U.S. PATENT DOCUMENTS

| | | | | |
|---|---|---|---|---|
| 2,940,300 | A | * | 6/1960 | Loving, Jr. ............... 73/35.17 |
| 3,942,357 | A | | 3/1976 | Jenkins |
| 4,585,932 | A | * | 4/1986 | Roberts et al. ............... 250/380 |
| 5,162,652 | A | * | 11/1992 | Cohen et al. ............... 250/288 |
| 5,274,356 | A | * | 12/1993 | Taricco ............... 340/515 |
| 5,345,809 | A | * | 9/1994 | Corrigan et al. ............... 73/23.2 |
| 5,367,552 | A | | 11/1994 | Peschmann |
| 5,420,905 | A | | 5/1995 | Bertozzi |
| 5,479,023 | A | | 12/1995 | Bartle |
| 5,600,303 | A | * | 2/1997 | Husseiny et al. ............... 340/568.1 |
| 5,692,029 | A | * | 11/1997 | Husseiny et al. ............... 378/88 |
| 5,784,430 | A | | 7/1998 | Sredniawski |
| 5,915,268 | A | * | 6/1999 | Linker et al. ............... 73/23.2 |

(Continued)

FOREIGN PATENT DOCUMENTS

WO 99/21148 A1 4/1999

(Continued)

OTHER PUBLICATIONS

*Aviation Week's Homeland Security & Defense* (Dec. 17, 2003)—"TSA to study portable 'sniffer' technologies".

(Continued)

*Primary Examiner* — Hezron E Williams
*Assistant Examiner* — Samir M Shah
(74) *Attorney, Agent, or Firm* — Innovation Counsel LLP

(57) ABSTRACT

A method and an apparatus for efficient resource sharing are presented. The apparatus includes a central unit having a plurality of surfaces on the outside, the central unit holding a resource. Compartments are coupled to the central unit, each of the compartments being placed adjacent to one of the surfaces of the central unit. Each compartment has a platform to support an object, and has a sensor that reads an output signal indicating that the object in the compartment has finished accessing the resource from the central unit. A computation unit receives and processes the output signal from each of the compartments. The sensor in the apparatus may be located in the central unit instead of in the compartments.

30 Claims, 8 Drawing Sheets

U.S. PATENT DOCUMENTS

| | | | |
|---|---|---|---|
| 6,073,499 A * | 6/2000 | Settles | 73/864.81 |
| 6,088,423 A | 7/2000 | Krug et al. | |
| 6,334,365 B1 * | 1/2002 | Linker et al. | 73/864.81 |
| 6,435,407 B1 * | 8/2002 | Fiordelisi | 235/383 |
| 6,545,945 B2 | 4/2003 | Caulfield | |
| 6,588,705 B1 * | 7/2003 | Frank | 244/118.5 |
| 6,610,977 B2 | 8/2003 | Megerle | |
| 6,656,334 B2 * | 12/2003 | Tseng et al. | 204/276 |
| 6,797,944 B2 * | 9/2004 | Nguyen et al. | 250/286 |
| 6,895,801 B1 | 5/2005 | Fine et al. | |
| 6,996,478 B2 * | 2/2006 | Sunshine et al. | 702/22 |
| 7,034,677 B2 * | 4/2006 | Steinthal et al. | 340/539.12 |
| 7,096,125 B2 * | 8/2006 | Padmanabhan et al. | 702/24 |
| 7,401,498 B2 * | 7/2008 | Syage et al. | 73/28.01 |
| 7,477,993 B2 * | 1/2009 | Sunshine et al. | 702/22 |
| 7,834,320 B2 * | 11/2010 | Goldberg et al. | 250/370.01 |
| 2001/0046275 A1 | 11/2001 | Hussein | |
| 2003/0085348 A1 * | 5/2003 | Megerle | 250/287 |
| 2003/0147484 A1 * | 8/2003 | Olshansky et al. | 376/157 |
| 2004/0064260 A1 * | 4/2004 | Padmanabhan et al. | 702/19 |
| 2004/0080315 A1 * | 4/2004 | Beevor et al. | 324/244 |
| 2004/0135684 A1 * | 7/2004 | Steinthal et al. | 340/522 |
| 2004/0181346 A1 * | 9/2004 | Sunshine et al. | 702/22 |
| 2005/0023445 A1 | 2/2005 | Horn et al. | |
| 2005/0057354 A1 * | 3/2005 | Jenkins et al. | 340/522 |
| 2005/0089140 A1 | 4/2005 | Mario et al. | |
| 2005/0104773 A1 * | 5/2005 | Clarke et al. | 342/357.09 |
| 2005/0124988 A1 * | 6/2005 | Terrill-Grisoni et al. | 606/53 |
| 2005/0237178 A1 * | 10/2005 | Stomski | 340/521 |
| 2006/0034726 A1 * | 2/2006 | Sunshine et al. | 422/58 |
| 2006/0087439 A1 * | 4/2006 | Tolliver | 340/573.1 |
| 2006/0139162 A1 * | 6/2006 | Flynn | 340/521 |
| 2006/0173656 A1 | 8/2006 | Hansen | |
| 2006/0243071 A1 * | 11/2006 | Sagi-Dolev | 73/865.8 |
| 2006/0249683 A1 * | 11/2006 | Goldberg et al. | 250/370.01 |
| 2007/0093970 A1 * | 4/2007 | Padmanabhan et al. | 702/23 |

FOREIGN PATENT DOCUMENTS

| | | |
|---|---|---|
| WO | 2004-023413 A2 | 3/2004 |

OTHER PUBLICATIONS

*PR Newswire* (Jun. 10, 2002)—HiEnergy Technologies, Inc., Detection System Performs Successfully in Blind Test at UCI: Systems Ability to Accurately Identify Explosives and Other Concealed Substances Could Provide Breakthrough in Counter-Terrorism Technology.

*Laser Focus World* (Apr. 1, 2003)—"Terahertz rays find new way to beef up security; . . . ".

*Business Wire* (Jun. 24, 2004)—"Smiths Detection Receives Order for X-Ray Baggage Screening Equipment from Greece".

International Search Report for PCT/US09/033122 dated Dec. 11, 2009 (2 pages).

Extended International Search Report and Opinion for EP 05 85 8411 dated Apr. 27, 2010 (8 pages).

* cited by examiner

APPARATUS FOR EFFICIENT RESOURCE SHARING

CROSS-REFERENCE TO RELATED APPLICATIONS

This patent application is a Continuation-in-Part of U.S. patent application Ser. No. 11/223,494 filed on Sep. 9, 2005, which claims the benefit of U.S. Provisional Patent Application No. 60/608,689 filed on Sep. 10, 2004 and U.S. Provisional Patent Application No. 60/680,313 filed on May 13, 2005. Contents of the provisional applications are incorporated by reference herein.

FIELD OF INVENTION

This invention relates generally to a system for detecting the presence of a threatening item, and more particularly to a system for detecting the presence of a threatening item using a plurality of tests in parallel.

BACKGROUND

Today, checkpoint security systems in public places like airports or government buildings typically include some combination of an imaging test, a metal detector, and a chemical test. The chemical test usually uses the table-top explosive trace detection (ETD) machine in which a swab or an air sample is taken from an object (e.g., a bag) and tested for trace explosive materials.

Unfortunately, the security check systems that are currently in use are not as reliable as they could be. For example, the X-ray tests identify threatening items based on object densities, and many innocuous objects have densities that are similar to those of some threatening items. Naturally, the rate of false-negative is high. With the imaging test involving X-ray or CT-scan, the accuracy of the test depends largely on the alertness and judgment of a human operator who reviews the images as the bags are scanned. While several systems include automatic visual classification of suspect items, reliance on human alertness and judgment still plays a major role in these systems. Due to distractions, fatigue, and natural limitation on human attention span, a check system that relies so heavily on human judgment cannot reach an optimal level of accuracy. Moreover, because imaging test relies heavily on the visualization of objects being tested, a passenger can disguise or hide a harmful threatening item and avoid detection by the imaging test.

Attempts have been made to increase the accuracy of a checkpoint security system by using a combination of tests, such as imaging, metal detector, and a chemical test. Typically, the tests are performed by utilizing three separate equipments and placing them next to one another. Objects are tested by the separate equipments separately and sequentially, one test after another. For example, an airport security system may employ an X-ray image test and subject only bags that are indicated as being suspect by the X-ray image test to a chemical test. Similarly, as for passengers, they may first be asked to pass through a preliminary metal detection portal, and be subjected to a more stringent metal detector test performed by a human operator only if an alarm is raised by the preliminary portal test.

A problem with this type of serial/sequential combination of tests is that the overall accuracy depends heavily on the accuracy of each individual test, and in some cases on the accuracy of the first test. For example, if the chemical test is not used unless a bag fails the X-ray imaging test, the use of the chemical test is only helpful if the X-ray imaging test accurately identifies the suspect bags. If the operator reviewing the X-ray images misses a potential threatening item, the fact that the chemical test is readily available does not change the fact that the potential threatening item passed through the security system.

While using multiple tests on every passenger and luggage would be an obvious way to enhance the accuracy of security checks, such solution is not practical because it would result in passengers spending an inordinate amount of time going through the security checks. Moreover, such system would be prohibitively costly. For a practical implementation, the accuracy of the security check tests is balanced by—and compromised by—the need to move the passengers through the system at a reasonable rate. Also, if a test that yields a high rate of false-positives like the X-ray test is used as the first test, the flow of passengers is unnecessarily slowed down because many bags that do not contain a threatening item would have to be subjected to the second test.

A system and method for moving the passengers through a security checkpoint at a reasonable rate without compromising the accuracy of the security check tests is desired.

SUMMARY

In one aspect, the invention is an apparatus for sharing a resource. The apparatus includes a central unit having a plurality of surfaces on the outside, the central unit holding a resource. Compartments are coupled to the central unit, each of the compartments being placed adjacent to one of the surfaces of the central unit. Each compartment has a platform to support an object, and has a sensor that reads an output signal indicating that the object in the compartment has finished accessing the resource from the central unit. A computation unit receives and processes the output signal from each of the compartments.

The sensor in the apparatus may be located in the central unit instead of in the compartments.

DETAILED DESCRIPTION OF THE EMBODIMENTS

Figure 1:
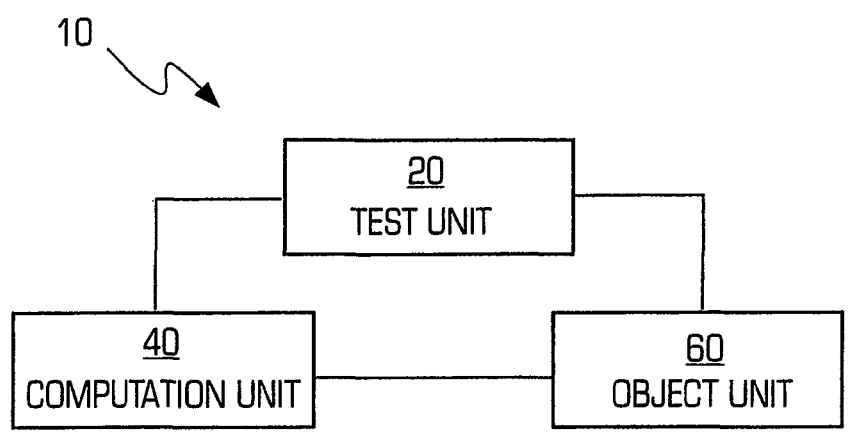
FIG. 1 is a block diagram illustrating the main components of a multi-threat detection system in accordance with the invention.

Embodiments of the invention are described herein in the context of a checkpoint security system. However, it is to be understood that the embodiments provided herein are just exemplary embodiments, and the scope of the invention is not limited to the applications or the embodiments disclosed herein. For example, the system of the invention may be useful for automated testing of small parcels and mail, non-security-related testing, and nondestructive testing for any purpose including checking packaged consumable items (e.g., food, drugs), among others.

The multi-threat detection system of the invention is useful for detecting the presence of various threatening items. A "threatening item" is any substance and or a combination of substances and objects that may be of interest to a security system including but not limited to explosives, explosive devices, improvised explosive devices, chemical warfare agents, industrial and other chemicals that are deemed hazardous, biological agents, contraband, drugs, weapons, and radioactive materials. The invention provides an automated system for performing different types of tests to screen multiple threatening items fast, such that multiple objects can be examined in a relatively short period of time. Furthermore, the system of the invention decreases the reliance on human operators, using instead a computation unit that determines a risk factor based on concurrent acquisition and processing of the different test results. Thus, the system provides the much-needed method of increasing the accuracy of a security check test without compromising the throughput.

An "ionized radiation test," as used herein, is intended to include any form of test that emits ionized radiation such as nuclear, X-ray, or Gamma ray radiation. Examples of X ray methods include standard X-ray transmission, backscatter methods, dual or multi energy methods as well as CT-scan. Examples of nuclear radiation source testing include methods such as Thermal Neutron Analysis, Pulsed fast neutron analysis, backscatter, and terahertz test, among others. A "non-ionizing test" includes methods that use a non-ionizing electromagnetic (EM) radiation source, such as those that expose the material to a pulsed EM field and acquire the return pulse. These methods include use of high-millimeter waves, Nuclear Magnetic Resonance (NMR) spectroscopy, Electron Spin Resonance (ESR) and Nuclear Quadrapole Resonance (NQR), among others. An additional potential non-ionizing source includes Tetrahertz. In addition, "non-ionizing tests" also include methods used in detection of conductive materials that subject an object to electromagnetic fields, either constant or pulsed wave, and detect the corresponding direction of changes in the field. "Chemical analysis" is intended to include methods of substance detection including ion mobility spectrometry (IMS), ion trap mobility spectroscopy (ITMS), capture detection, chemiluminescence, gas chromatography/surface acoustic wave, thermo-redox, spectroscopic methods, selective polymer sensors, and MEM based sensors, among others.

A "biological classification" classifies biological threats (e.g., organisms, molecules) according to guidelines indicating the potential hazard level associated with toxins, bioregulators, and epidemically dangerous organisms (such as viruses, bacteria, and fungi). A "biometric classification test" includes standard discrete biometric methods such as finger prints, as well as physio-behavioral parameters indicative of suspect behavior.

As used herein, "simultaneously" is intended to mean a partial or a complete temporal overlap between two or more events of the same or different durations. For example, if Event A begins at time 0 and ends at time 10 and Event B begins at time 2 and ends at time 10, Event A and Event B are occurring simultaneously. Likewise, Event C and Event D that both start at time 0 and end at time 7 are also occurring simultaneously. "Sequentially," on the other hand, indicates that there is no temporal overlap between two or more events. If Event E begins at time 0 and ends at time 6 and Event F begins at time 7 and ends at time 10, Events E and F are occurring sequentially.

A "parameter," as used herein, is intended to include data and sets of data and functions, either static or dynamic.

A "threat determination function," as used herein, is intended to include a function or sets of functions that define a condition that indicates the presence of a threat. Theses function(s) can be a static value, sets of static values, or a dynamic calculation. The function(s) can be either rule-based or based on other methods such as neural network.

A "risk factor" indicates the likelihood that the threatening item is present in the object. A "set" of risk factors may include one or more risk factors.

FIG. 1 is a block diagram illustrating the main components of a multi-threat detection system 10 in accordance with the invention. As shown, the multi-threat detection system 10 includes a test unit 20, a computation unit 40, and an object unit 60 that are coupled to one another. The object unit 60 has a mechanism that is designed to hold an object (e.g., a bag or a piece of luggage) that is being examined. The test unit 20 includes various test sources and/or equipment such as a radiation source for an X-ray exam, a chemical analysis unit for a chemical exam, RF coils and or other magnetic field inductions for a non-ionizing exam. The computation unit 40, which has a processor and a memory, is configured to receive inputs from the test unit 20 and the object unit 60 and process the inputs to generate a risk factor. The risk factor indicates the likelihood of the object in the object unit 60 containing a threatening item. Optionally, there may be a communication unit that may include a user interface unit (not shown) that is coupled to the computation unit 40 so that the risk factor and a corresponding alert can be communicated to an operator of the multi-threat detection system.

The tests that are incorporated into the test unit 20 may be any currently known tests for screening threatening items, and is not limited to the examples mentioned herein. There may also be a plurality of object units coupled to the test unit 20 and the computation unit 40 so that multiple objects can be examined almost at the same time.

Figure 2:
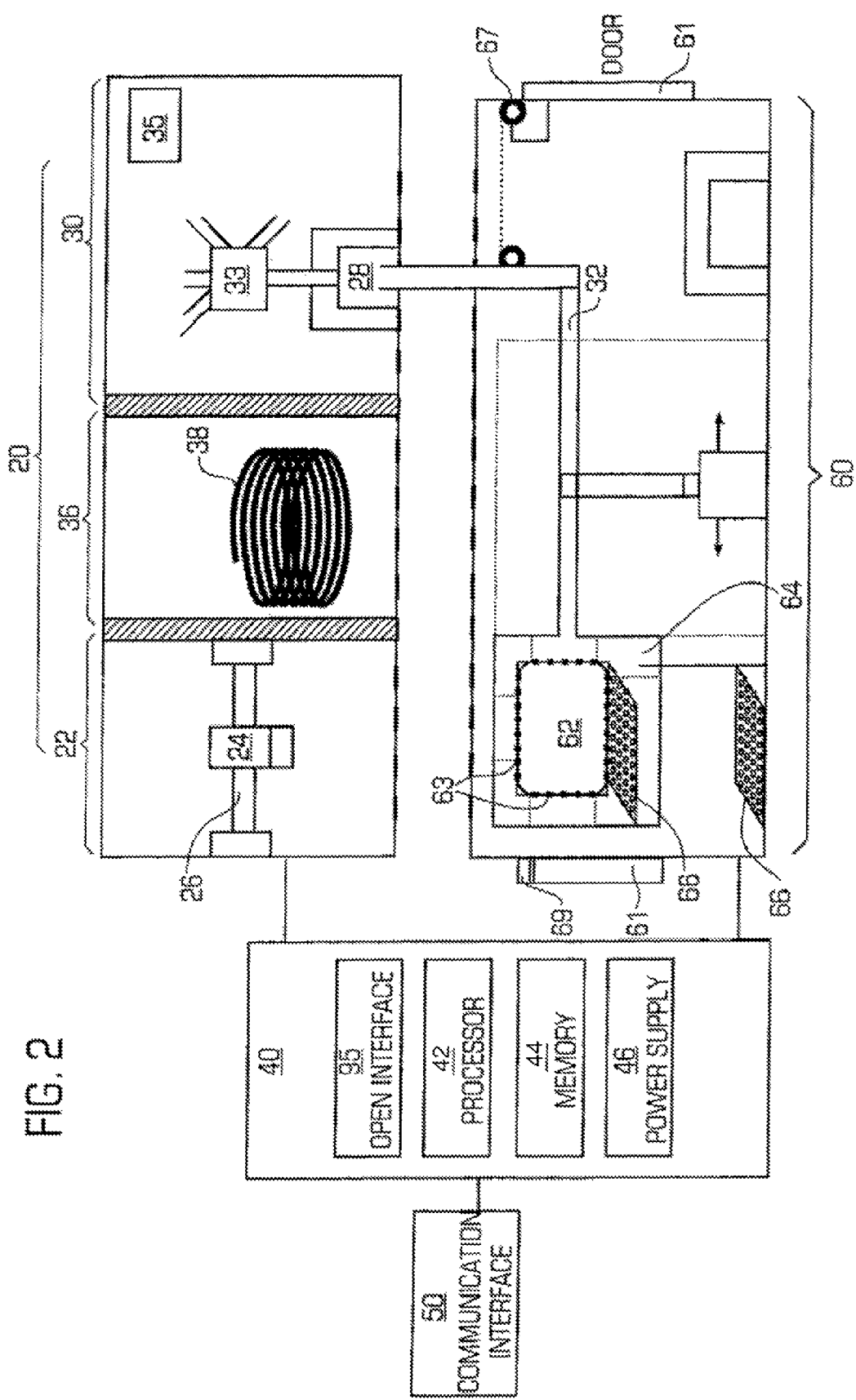
FIG. 2 is a block diagram of an exemplary embodiment of the multi-threat detection system.

FIG. 2 is a block diagram of an exemplary embodiment of the multi-threat detection system 10.

The object unit 60 has one or more doors 61 through which an object 62 can be placed in the object unit 60 to be subjected to various tests. In some embodiments, the object 62 remains stationary on a platform in the object unit 60. In other embodiments, the object 62 is moved across the object unit 60 through a moving mechanism 67. The moving mechanism 67 may be coupled to a grasping and/or rotating mechanism 64, which may be a robotic mechanism that is capable of holding the object 62 and positioning and rotating the object 62 in a desired location at the desired test angle. In the embodiment shown, the moving mechanism 67 is a type of pulley system, an x-y positioner system 65, a linear motor, or any combination of these systems, and is coupled to the grasping and/or rotating mechanism 64. In an alternative embodiment, the moving mechanism may be a conveyor belt that carries the object 62 through different test stages.

The object unit 60 includes an automated receiver 69 that automatically provides extra information about the owner of the object 62. In some embodiments, the extra information may include ticketing information. In other embodiments, additional information about the owner, such as his name, citizenship, travel destination, etc. may also be made available by the automated receiver 69. The automated receiver 69 may be implemented with digital/magnetic tagging, RF tagging, or other smart card scan that identifies the owner/carrier of the object 62. This automatic correlation between the object 62 and its owner/carrier facilitates identifying the responsible person if a threatening item is found. The object unit 60 has one or more doors 61 through which the object can be removed. In some embodiments, the doors 61 are locked automatically upon the identification of a threatening item as part of the operational security protocols.

In this exemplary embodiment, the ionized radiation test unit 20 has an X-ray source subunit 22, a chemical analysis subunit 30, and non-ionizing source subunit 36. The X-ray examination is done by an X-ray source 24 generating a beam and directing it toward the object 62. The X-ray source 24 is preferably supported by a rotating mechanism 26 that allows the beam to be pointed in different directions, as it may be desirable to adjust the direction of the beam according to the size and the position of the object 62. A plurality of sensors 66 are located in the object unit 60 and positioned to receive the X-ray beams after they pass through the object 62. Additional sensors 66 can be positioned to acquire back scatter radiation as well. The beam is received by the sensors 66 after passing through the object 62. The sensors 66 generate output signals based on the received beam and feed the output signals to the computation unit 40. Where X-ray is used as one of the tests, the walls of the X-ray subunit 22 and the object unit 60 are shielded to contain the radiation within the object unit 60.

The chemical analysis may be performed by taking a sample from the object 62 and running the sample through the chemical analysis subunit 30. A path implemented by a flow device such as a rotational flow device 32 connects the grasping and/or rotating mechanism 64 to the chemical analysis subunit 30 so that the sample from the object 62 can be transported to the chemical analysis subunit 30. The chemical analysis may be based on, for example, ion mobility spectroscopy, or newer methods such as selective polymers or MEMs-based sensors. Where ion mobility spectroscopy is used, the chemical analysis subunit 30 includes an ionization reaction chamber 28. An air flow is generated by a vacuum pump 33 for obtaining a gas sample from the object unit 60. The gas sample travels through the adjustable closure pipes 32, which have particle acquisition pores 63 in proximity to the object 60 for obtaining gas samples. The rotational flow device 32 and the particle acquisition pores 63 provide a means for continuous-contact gas agitation and particle acquisition for continual analysis while the object moves inside the object unit 60 for other tests. The particle acquisition pores 63 may be placed on the grasping and/or rotating mechanism 64 that moves the object 62 across the object unit 60, such as the robotic arm or the conveyor belt mentioned above. The gas sample enters the chemical analysis subunit 30. In an exemplary embodiment using the IMS method, the gas sample enters an ionization reaction chamber 28 through the rotational flow device 32 and becomes ionized by an ionization source. The ionized gas molecules are led to a collector plate (not shown) located in the ionization reaction chamber 28 by an electric field within the chamber 28. The quantity of ions arriving at the collector plate as a function of time is measured and sent to the computation unit 40 in the form of one or more output signals. A microprocessor at the chemical analysis subunit 30 may convert the quantity of ions to a current before sending the current to the computation unit 40. IMS is a well-established method.

Optionally, the chemical analysis subunit 30 contains an interfacing module 35 to a biological detection system. If a biological detection system is incorporated into the test unit 20, a biological classification of the object can be obtained. A biological detection system that detects molecular materials could utilize one of the chemical analysis methods. A system that is intended to identify an organism, such as Anthrax, would utilize an automated DNA testing based on automated polymerase chain reaction (PCR) according to the current state of technology.

The non-ionizing source subunit 36 may contain a radiofrequency (RF) source and/or a magnetic source, such as RF coils 38 and antennae for NQR testing and/or eddy current testing. These tests provide information on the chemical compositions of the object and or information on the existence of metallic and other conductive materials. Magnetic sources may be a plurality of sources that vary in size and strength, so that the location of a threatening item can be detected as well as its presence. Radiofrequency waves and/or a magnetic field is directed at the object 62 and the sensors 66 receive the wave and/or the field after it passes through the object 62. For example, where the subunit 36 is a metal detector, the metal detector may transmit low-intensity magnetic fields that interrogate the object 62 as it passes through the magnetic fields. A transmitter generates the magnetic field that reacts with the metal objects in its field and the sensors 66 measure the response from this reaction. The sensors 66 send the measurement result to the computation unit 40.

In addition to the X-ray exam, ion mobility spectrometry, and the non-ionizing source test used in the embodiment of FIG. 2, any other test may be employed by the multi-threat detection system 10 if considered useful for the particular application. Also, the X-ray exam, the ion mobility spectrometry, and the non-ionizing source test may be substituted by different tests as deemed fit by a person skilled in the art. Preferably, each of the subunits 22, 30, 36 is designed to be replaceable independent of other subunits. Thus, substituting one test with another will likely be a matter of replacing one subunit with another.

The sensors 66 may be a fused-array sensor capable of collecting multiple information either in parallel or in a multiplexed manner. Information collected may include any test results such as X-ray, terahertz ray, gamma ray, RF, chemical, nuclear radiation, and current information.

The computation unit 40 includes a processor 42, a memory 44, and a power supply 46. Using a multi-variant method such as the method described below in reference to FIG. 3, the computation unit 40 determines the risk factor, which indicates the likelihood that an object will contain a threatening item. The computation unit 40 has a communication interface 50 through which it can send visual and/or audio alerts in any mode of communication, preferably wirelessly, if an object is likely to contain a threatening item. There is also at least one open interface 95 that allows the computation unit 40 to communicate with another apparatus, such as a platform for human portal system or a platform for biometric inputs. The open interface 95 may allow wired or wireless connections to these other apparatuses.

The chemical analysis test results may be sent directly from the collector plate in the chemical analysis subunit 30 to the computation unit 40. If desired, however, the data from the collector plate may be sent to one or more sensors 66 in the object unit 60 and sent to the computation unit 40 indirectly from the sensors 66. When using other methods such as passive sensors, particles can be routed directly to sensors 66. Other data, such as X-ray data, are collected by the sensors 66 and sent to the computation unit 40. As used herein, "sensors" include any type of device that is capable of making a physical or electrical measurement and generating an output signal for the computation unit 40, such as sensors 66 in the object unit 20 and the collector plate in the chemical analysis subunit 30.

Although FIG. 2 shows the test unit 20, the computation unit 40, and the object unit 60 as three separate components, the division is conceptual and the physical units do not necessarily have to correlate with the conceptual division. For example, all three units may be contained in one housing, or the test unit 20 and the object unit 60 may be contained in the same housing while the computation unit 40 is in a remote location.

Figure 3:
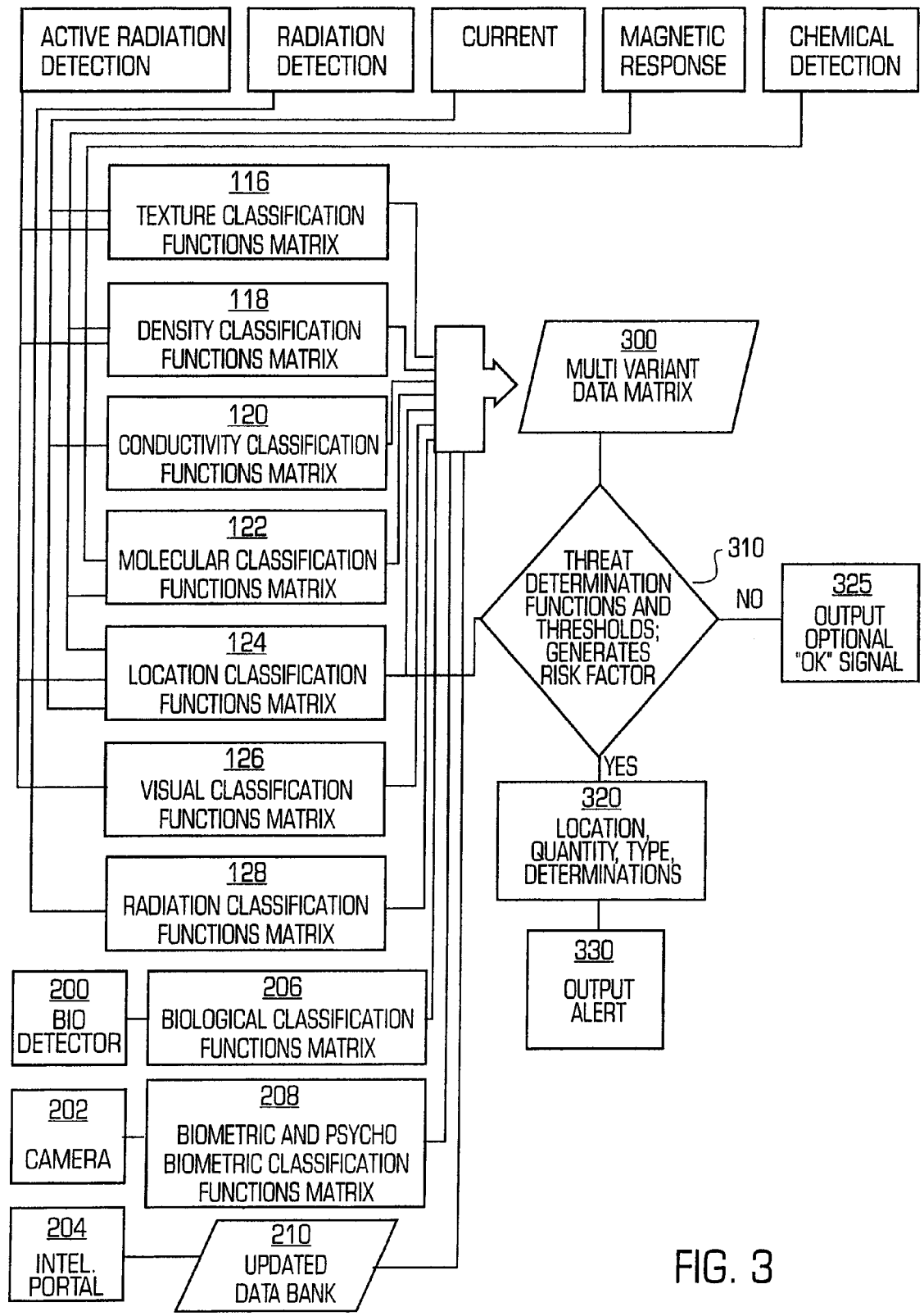
FIG. 3 is a block diagram illustrating the modules of the computation unit for executing a threatening item identification method.

FIG. 3 is a block diagram illustrating the modules of the computation unit 40 for executing a threatening item identification method. As described above, the computation unit 40 receives inputs from the test unit 20 and/or the object unit 60. These inputs originate as raw data collected by the sensors 66 and/or the collector plate in ion mobility spectrometry (or another chemical sensor). As shown in the diagram, the method of the invention uses a set of functional modules 116, 118, 120, 122, 124, 126, 128, 206, 208 to process the various inputs from the sensors 66 and the sensor in the test unit 20 (e.g., the collector plate). Using these modules, values are calculated for various parameters such as texture, density, electrical conductivity, molecular classification, location classification, radiation classification, visual classification, biological classification, and biometric classification for the object 62. Where the object 62 is something like a bag that contains multiple components, the components may be automatically divided according to texture, density, conductivity, etc. so that each component is classified separately.

In the particular embodiment of the threatening item identification method that is shown in FIG. 3, the active radiation (e.g., X-ray) detection results are used for determination of texture classification, density classification, shape context classification, location classification, and visual classification. The radioactive level of the object may be determined for radiation classification. Current data or induced EM field responses are used for parameters such as texture classification, conductivity classification, and location classification. The magnetic response is used for calculating parameters such as molecular classification, density classification, and location classification. Any chemical analysis result is used for molecular classification. Output signals from the sensors 66 and output signals from the chemical analysis subunit 30 are fed to the different modules in parallel, so that the values for all the parameters of the classification areas such as texture, density, etc. can be determined substantially simultaneously.

After the parameters based on values and functions for each of these classification areas is determined, the values are collectively processed in a multi-variant data matrix module 300 to generate a risk factor. The multi-variant data matrix 300 arranges the plurality of classification parameters from function matrices 116, 118, 120, 122, 124, 126, 128, 206, 208, 210 into an n-dimensional data matrix. For instance, visual classification function matrix 124 would yield numerous visualization data [V] as a function of number of (1 . . . n) and measurement and angles (101) depending on the number of rotations performed by the grasping and/or rotating mechanism 64, so one form of data would be V=f($\Phi$)n. Additionally, a series of visualization data [V] related to density parameters [D] at each angle $\Phi$ would yield the set of parameters V=f(D, $\Phi$, n). Another set of parameters fed into the multi-variant data matrix 300 would be conductivity classifications from the conductivity classification functions matrix 120 and would similarly yield an array of interrelated parameters, for example conductivity [Z] as having varying intensities (i) as a function of location (l) yielding one set of Z=f(i,l). These three exemplary functions V=f($\Phi$, n), V=f(D, $\Phi$, n), and Z=f(i,l) would be arranged in the multi variant data matrix 300 in such a way that provides multiple attributes for particular three-dimensional locations, as well as global attributes, throughout the screened object. More generally, all classification function matrix blocks will produce numerous parameter sets, so that an n-dimensional parameter matrix is produced for processing in block 310.

The n-dimensional parameter matrix generated in block 310 enables numerous calculations and processing of dependent and interdependent parameters to be performed in block 310. The parameters from the multi-variant data matrix module 300 is submitted to the threat determination functions, which include running sets of hybrid calculations. Hybrid calculations include combinations of rule-based and other methods (such as neural network or other artificial intelligence (AI)-based algorithms) and comparison of the result against real-world knowledge criteria and conditions (block 310). In some embodiments, an example of a rule-based decision would combine testing some or all of the parameter(s) against thresholds. For example, a condition such as "If texture classification T($\Phi$,L)n>3, density classification D($\Phi$, L)n>4, conductivity classification Z(i,l)n>4, location classification>3, and radiation classification>1" could be used as a condition for determining one type of risk factor and possibly generating an alert. Calculations may be any simple or complex combination of the individual parameter values calculated by test block 310 to determine sets of risk factors. Sets of risk factors represent various categories of threats that are likely to be present in the object. For instance, there may be a category of threat functions associated with the likelihood of a biological event which would produce a risk factor for this category, there may also be a category of threat functions associated with the likelihood of an explosive threat which would produce a risk factor for the explosive category, and yet there may be a category threat functions associated with a general likelihood evoked by a combination of attributes not necessarily specifically to the material type. Different calculations may yield a number of risk factors within each category. The threat functions include test conditions and apply criteria based on pre-existing real world knowledge on signals and combinations of signals identifying threats.

If a high-enough risk factor is determined that the preset set of threat thresholds are satisfied, depending on the embodiment, the location, quantity, and type of the threatening item may be estimated (block 320), an alert may also be generated (block 330). Whether a risk factor is high enough to trigger the alert depends on the sensitivity settings within the system, which has a default setting and is reconfigurable by the user. An "alert" may include a visual or audio signal for notifying the operator that a threatening item may have been identified, and may also include taking other operational actions such as closure/locking of the door 61 in the object unit 60. Optionally, a signal (e.g., a green light) may be generated to indicate that an object is clear of threatening items (block 325).

Figure 4:
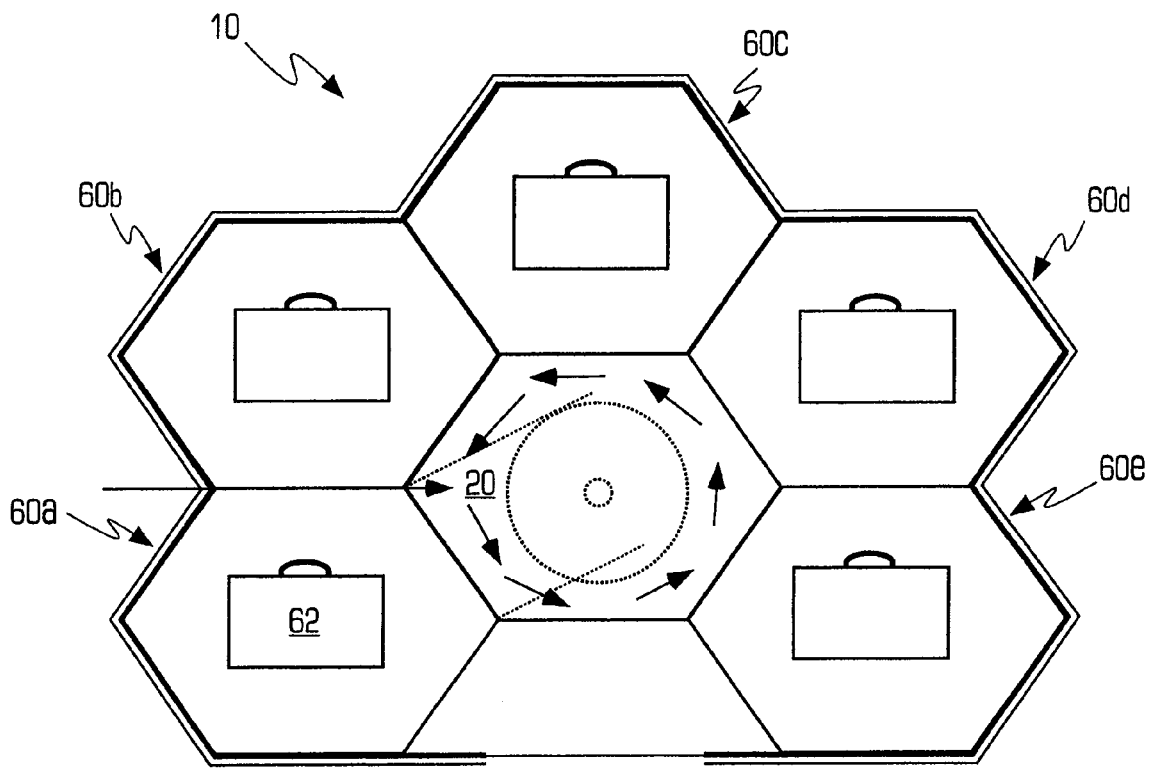
FIG. 4 is an exemplary embodiment of the multi-threat detection system including a single test unit and multiple object units, wherein the test unit has flat outer surfaces.
Figure 8:
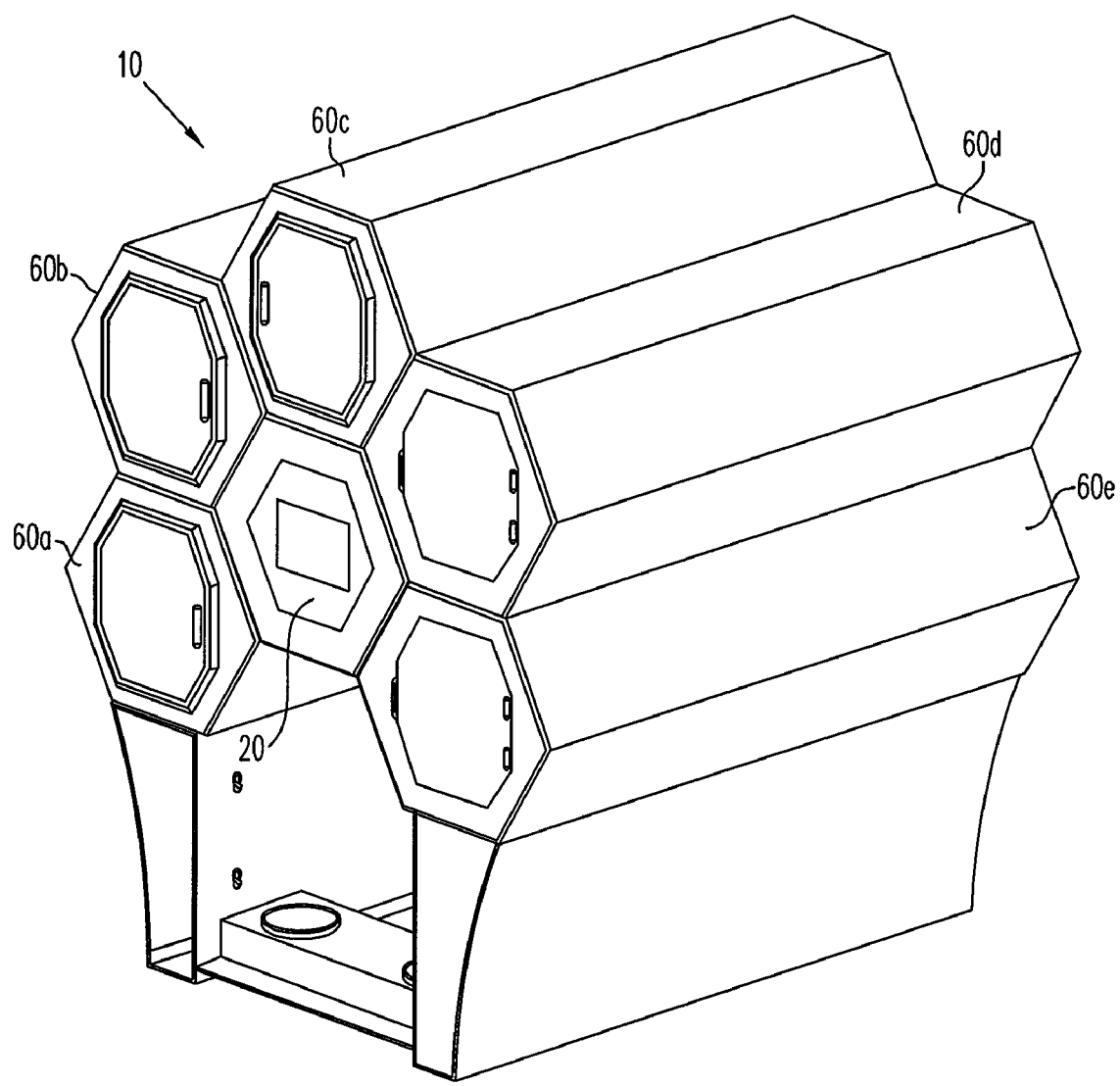
FIG. 8 is a perspective view of an exemplary embodiment of the multi-threat detection system including a single test unit and multiple object units.

FIG. 4 is a cross-sectional view of an exemplary embodiment of the multi-threat detection system 10 including a single test unit 20 and multiple object units 60a-60e. FIG. 8 is a perspective view of the system 10. In this embodiment, the centrally located test unit 20 has flat outer surfaces that interface the object units 60a-60e. As shown, the test unit 20 is located centrally with respect to the object units 60 so that an object can be tested by the test unit 20 regardless of which object unit it is in. The test unit 20 and the object unit 60 may be made of any material with structural integrity including various metals (e.g., steel) or composite material. Preferably, there is a rotating mechanism in the test unit 20 that allows the direction of the test beam, etc. to be adjusted depending on which object is being tested. Once all the object units are filled, the test unit performs tests on the objects by turning incrementally between each object unit 60 as shown by the arrows. Some tests are performed sequentially. For example, if an X-ray test is performed, the X-ray beam is directed from the test unit 20 to the multiple object units 60a-60e sequentially, e.g. in a predetermined order. However, other tests are performed simultaneously for the multiple object units 60a-60e. For example, if a chemical analysis test is performed, a sample of each object in the multiple object units 60a-60e can be taken simultaneously, as each object unit has its own rotation flow device 32, grasping and/or rotating mechanism 64, and particle acquisition pores 63. Thus, depending on the tests that are included in the particular embodiment, the overall testing may be partly sequential and partly simultaneous for the multiple object units 60a-60e. All the test data are sent to the computation unit 40, preferably as soon as they are obtained.

The output signals from the sensors 66 (and the collector plate of the chemical analysis subunit 30, if applicable) may be processed by a single computation unit 40 or a plurality of computation units 40. Where a single computation unit 40 is used, the computation unit 40 keeps the objects separate so that it yields five different results, one for each object 62.

The embodiment of FIG. 4 allows multiple objects to be processed quickly compared to the current security check system where passengers form a single line and one object (e.g., bag) is processed at a time. Therefore, all the tests incorporated into the test unit 20 can be performed for each of the objects in the object units 60a-60e without compromising the traffic flow.

The multi-threat detection system 10 of FIG. 4 may be designed as a modular unit, so that the number of object units 60 is adjustable. Thus, if a first area is getting heavy traffic while traffic in a second area has slowed down, a few of the object units from the second area can be used for the first area by simply being detached from one test unit 20 and being attached to another test unit 20. The detaching-and-attaching mechanism may use hook systems and/or a clasping/grasping/latching mechanism. This flexibility results in additional cost savings for public entities that would use the multi-threat detection system 10. The object units 60a-60e are substantially identical to one other.

Additionally, the platform on which the object 62 is placed in the object unit 60 may have a sensor, such as a weight or optical sensor, that signals to the test unit 20 whether the particular object unit 60 is in use or not. So, if only object units 60a, 60b, 60d, and 60e are used for some reason, the test unit 20 will not waste time sending test beams and collecting samples from the empty object unit 60c and the system 10 will automatically optimize its testing protocols. The system 10 may include a processor for making this type of determination. A sensor is placed either in each object unit 60 or in the test unit 20 to detect an output signal indicating that an object in the object unit 60 has been tested.

Figure 9:
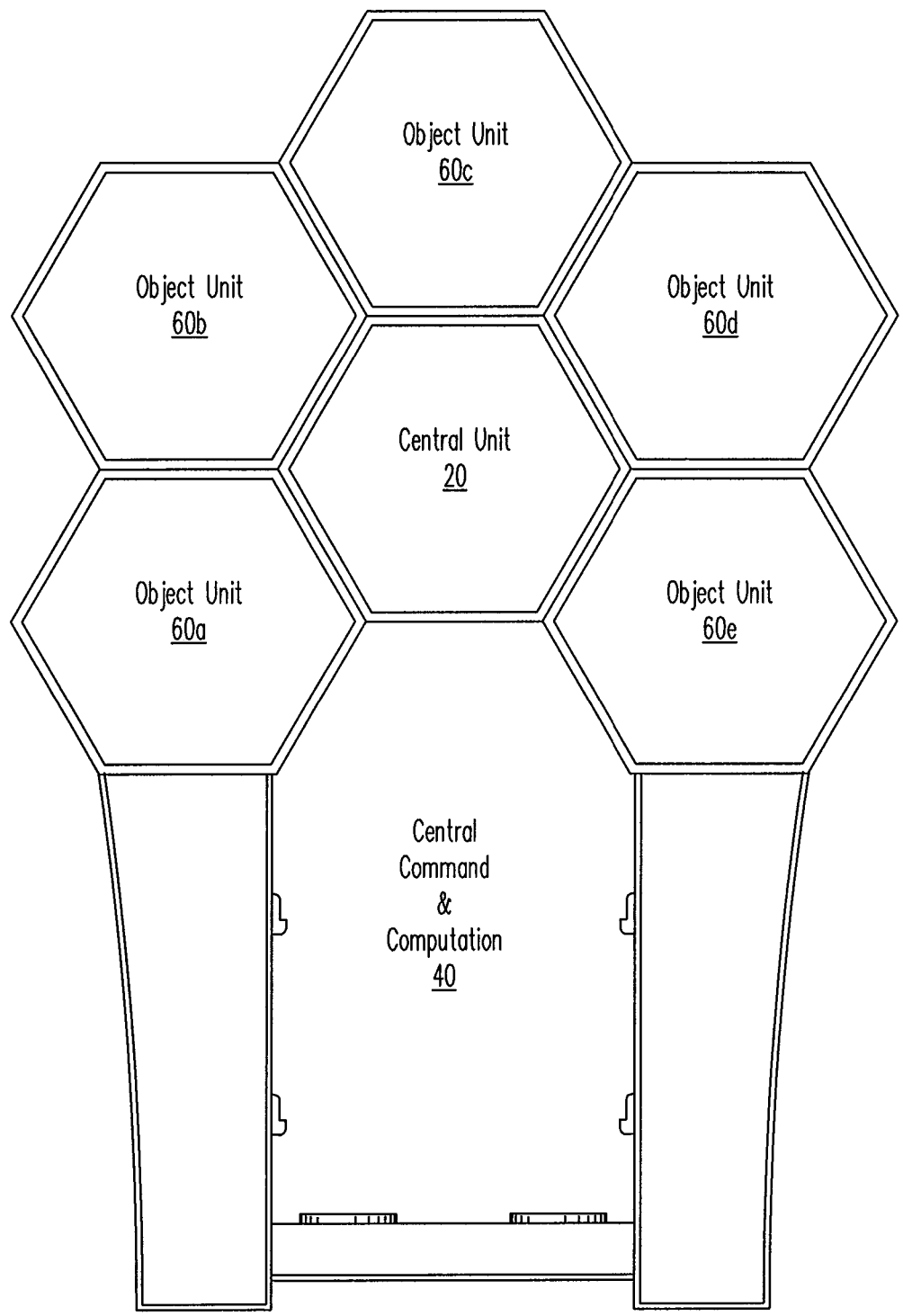
FIG. 9 is a cross-sectional view of an alternative embodiment of the multi-threat detection system wherein the central unit has a curved outer surface.

Although the particular embodiment shows the units as having hexagonal shapes for a honeycomb configuration, this is just an example and not a limitation of the invention. For example, the test unit 20 may have any polygonal or curved cross section other than a hexagon. FIG. 9, for example, shows a cross-sectional view of a multi-threat detection system 10 wherein the test unit 20 has a curved outer surface (as opposed to flat outer surfaces as in the embodiment of FIG. 4). The shapes of the object units 60a-60e are adapted so they can efficiently and securely latch onto the test unit 20. Furthermore, the structure allows a resource in a central unit (e.g., the test unit 20) to be shared among the surrounding compartments (e.g., object units 60) in a fast and space-efficient manner, making the structure useful for various applications other than detection of threatening objects. For example, where multiple objects need to be encoded with a piece of data, the data source can be placed in the central unit so that objects in the surrounding compartments can read the data. In a case of laser etching, objects in the compartments could receive data encoding from the central unit.

Figure 5:
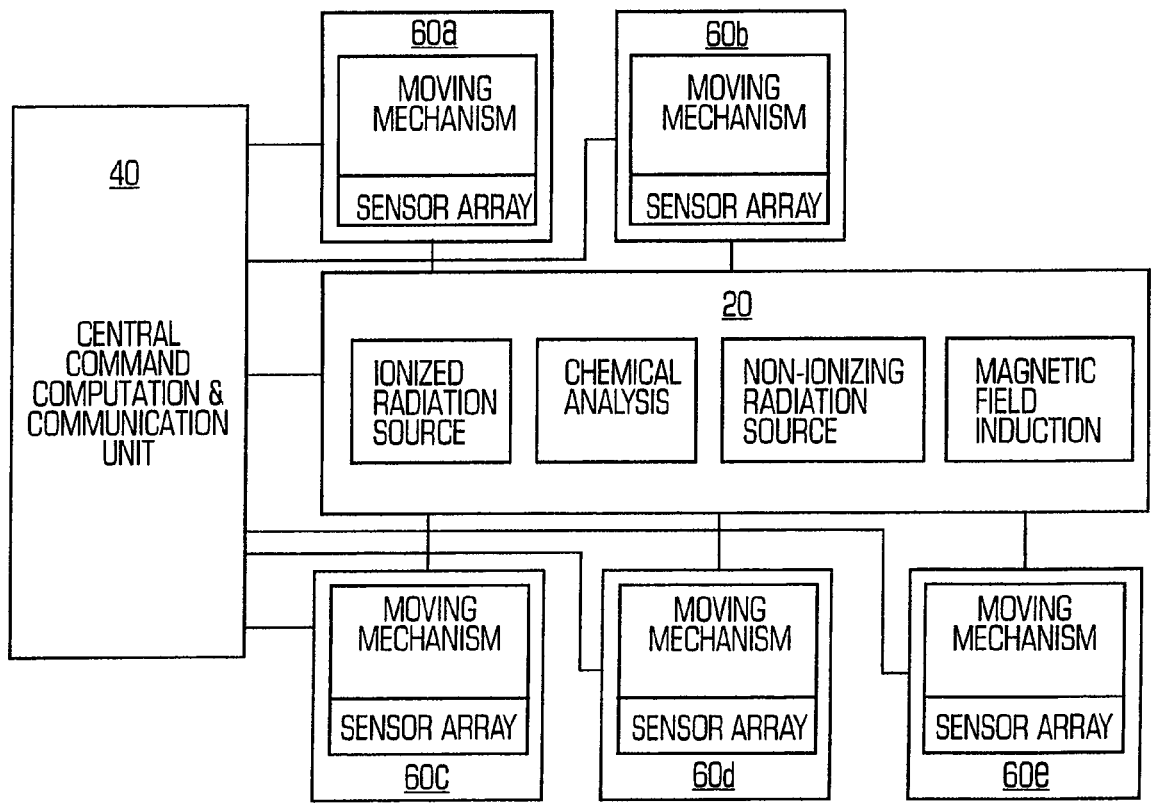
FIG. 5 is a block diagram showing the test unit and the object units.

FIG. 5 is a block diagram showing the test unit 20 and the object units 60a-60e. In the particular embodiment, a single computation unit 40 is used for all the object units 60a60e. Each of the object units 60a-60e contains a moving device, such as a mechanical mechanism, multi axis manipulator, robotic mechanism, a conveyor belt, or any other rotating and linear mechanism and a sensor array, as described above in reference to FIG. 2. The moving device allows both linear and rotational movement. The test unit 20 has four subunits: an ionized radiation source subunit, a chemical analysis subunit, a non-ionizing radiation source subunit, and a magnetic field induction subunit. Each of the object units 60a-60e is coupled to the test unit 20 and the computation unit 40.

Figure 6:
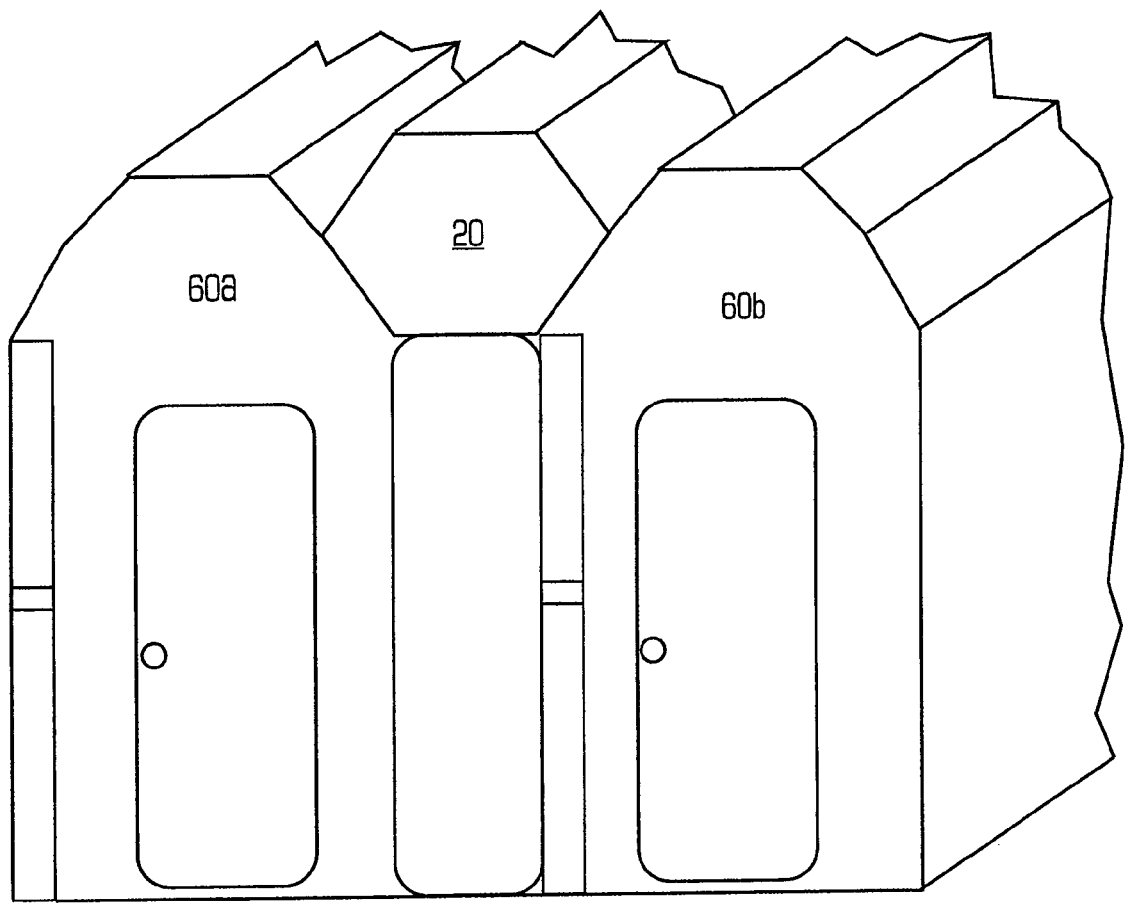
FIG. 6 is another exemplary embodiment of the multi-threat detection system wherein the object is a human being (or any of other animals).

FIG. 6 is another exemplary embodiment of the multi-threat detection system 10 wherein the object is a human being (or any of other animals). In the particular embodiment that is shown, the test unit 20 has two object units 60a, 60b attached to it. Naturally, tests involving radiation will be used with caution, by choosing appropriate radiation sources and parameters when the "objects" being tested are human beings. If desired, a camera may be installed somewhere in the test unit 20 or the object unit 60a and/or 60b to obtain images of objects in order to obtain a biometric classification and/or transmit images to an operator.

Figure 7:
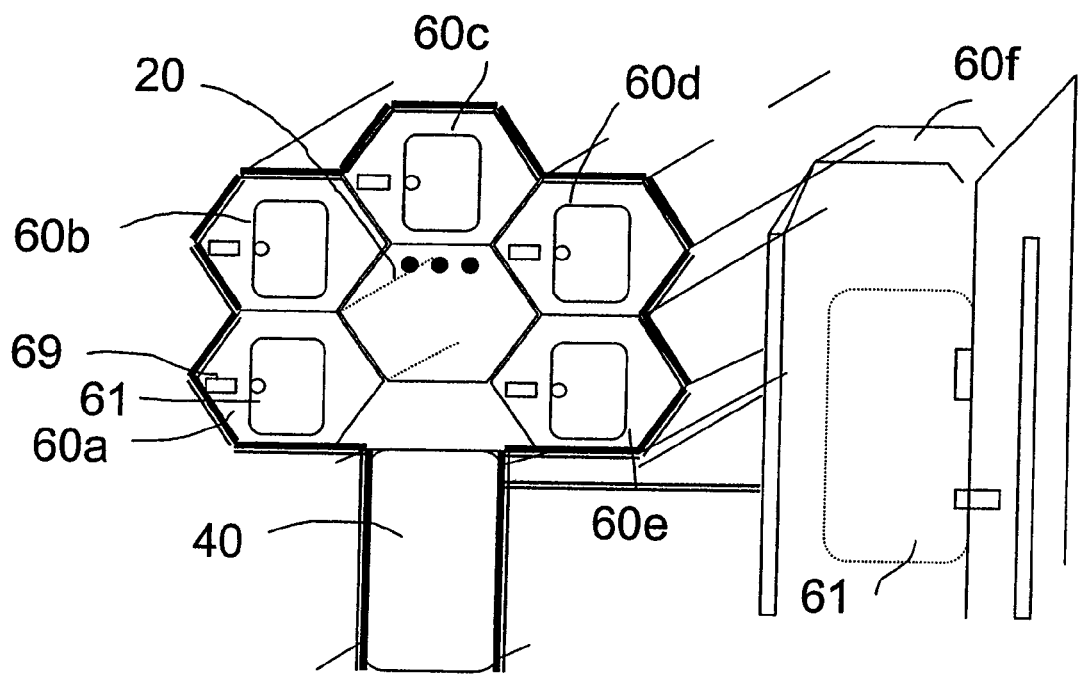
FIG. 7 is yet another exemplary embodiment of the multi-threat detection system for testing inanimate objects and human beings.

FIG. 7 is yet another exemplary embodiment of the multi-threat detection system 10 for testing inanimate objects and human beings. The particular embodiment has the test unit 20 with five object units 60a-60e for testing inanimate objects and a portal 60f for human beings or animals to pass through. The test unit 20 tests objects in the object units 60a-60e and human beings in the object unit 60f that are in each of the object units 60a-60f. However, all the object units and both test units would still feed signals to a single computation unit 40.

The invention allows detection of threatening items with increased accuracy compared to the currently available system. While the currently available systems use a sequence of separate equipment, each equipment using only one test and generating a test result based only on that one test, the system of the invention relies on a combination of a plurality of parameters. Thus, while a bomb that has a low level of explosive and a small amount of conductive material may escape detection by the current system because both materials are present in amounts below the threshold levels, the object could be caught by the system of the invention because the presence of a certain combination of indicative materials and vicinity parameters included in the threat determination functions could trigger an alarm. The use of combinations of parameters allows greater flexibility and increased accuracy in detecting the presence of threatening items.

The invention also allows detection of a general threatening item, material deformation, and fractures in the case of a nondestructive testing. This is different from the current system that targets specific items/materials such as explosives, drugs, weapons, etc. By detecting the presence of a general combination of potentially hazardous materials, the system of the invention makes it more difficult for creative new dangerous devices to pass through the security system.

While the foregoing has been with reference to particular embodiments of the invention, it will be appreciated by those skilled in the art that changes in this embodiment may be made without departing from the principles and spirit of the invention.

What is claimed is:

1. An apparatus for sharing a resource, the apparatus comprising:
   a central unit having a plurality of outer surfaces, the central unit holding the resource;
   a plurality of compartments coupled to the central unit, each of the compartments placed adjacent to one of the outer surfaces of the central unit and having a platform to support an object;
   a sensor located in each of the compartments, wherein the sensor reads an output signal indicating that the object in the respective compartment accessed the resource in the central unit; and
   a computation unit receiving and processing the output signal from each of the compartments;
   wherein the resource is at least one of test source useful for testing the object, data, and equipment.

2. The apparatus of claim 1, wherein the compartments access the resource simultaneously.

3. The apparatus of claim 1, wherein the compartments access the resource sequentially.

4. The apparatus of claim 1, wherein the central unit comprises a rotating mechanism for directing the resource to a selected one of the compartments.

5. The apparatus of claim 1, wherein the central unit has a polygonal cross section.

6. The apparatus of claim 5, wherein the central unit has a hexagonal cross section.

7. The apparatus of claim 1, wherein the compartments are modular and detachably engaged with the central unit.

8. The apparatus of claim 1, wherein the resource comprises a radiation source for testing objects in the compartments.

9. The apparatus of claim 1, wherein the resource comprises a magnetic field induction unit.

10. The apparatus of claim 1, wherein the resource comprises stored data to be read by objects in the compartments.

11. The apparatus of claim 1, wherein each of the compartments comprises a mechanism for moving an object into and out of the compartment.

12. The apparatus of claim 1, wherein each of the compartments comprises a weight sensor for detecting the presence of an object, and wherein the central unit comprises:
   a detector reading each weight sensor; and
   a processor determining which compartments to direct the resource at.

13. The apparatus of claim 1, wherein the central unit holds a plurality of different resources.

14. The apparatus of claim 1, wherein the outer surfaces of the central unit are flat and each of the compartments has at least one flat surface that is coupled to one of the outer surfaces of the central unit.

15. The apparatus of claim 1, wherein the outer surfaces of the central unit are curved and each of the compartments has at least one curved surface that is coupled to one of the outer surfaces of the central unit.

16. An apparatus for sharing a resource, the apparatus comprising:
   a central unit having a plurality of outer surfaces, the central unit holding a resource;
   a plurality of compartments coupled to the central unit, each of the compartments placed adjacent to one of the outer surfaces of the central unit and having a platform to support an object;
   a sensor located in the central unit, wherein the sensor reads an output signal from each of the compartments indicating that the resource has been accessed by the compartment; and
   a computation unit receiving and processing the output signal from each of the compartments;
   wherein the resource is at least one of test source useful for testing the object, data, and equipment.

17. The apparatus of claim 16, wherein the compartments access the resource simultaneously.

18. The apparatus of claim 16, wherein the compartments access the resource sequentially.

19. The apparatus of claim 16, wherein the central unit comprises a rotating mechanism for directing the resource to a selected one of the compartments.

20. The apparatus of claim 16, wherein the central unit has a polygonal cross section.

21. The apparatus of claim 20, wherein the central unit has a hexagonal cross section.

22. The apparatus of claim 16, wherein the compartments are modular and detachably engaged with the central unit.

23. The apparatus of claim 16, wherein the resource comprises a radiation source for testing objects in the compartments.

24. The apparatus of claim 16, wherein the resource comprises a magnetic field induction unit.

25. The apparatus of claim 16, wherein the resource comprises stored data to be read by objects in the compartments.

26. The apparatus of claim 16, wherein each of the compartments comprises a mechanism for moving an object into and out of the compartment.

27. The apparatus of claim 16, wherein each of the compartments comprises a weight sensor for detecting the presence of an object, and wherein the central unit comprises:
   a detector reading each weight sensor; and
   a processor determining which compartments to direct the resource at.

28. The apparatus of claim 16, wherein the central unit holds a plurality of different resources.

29. The apparatus of claim 16, wherein the outer surfaces of the central unit are flat and each of the compartments has at least one flat surface that is coupled to one of the outer surfaces of the central unit.

30. The apparatus of claim 16, wherein the outer surfaces of the central unit are curved and each of the compartments has at least one curved surface that is coupled to one of the outer surfaces of the central unit.

* * * * *